(12) United States Patent
Dabkowski et al.

(10) Patent No.: US 7,541,320 B2
(45) Date of Patent: Jun. 2, 2009

(54) MILD, VISCOUS CLEANSING COMPOSITION WITH VERSATILE COMPATIBILITY AND ENHANCED CONDITIONING

(75) Inventors: Diane Maria Dabkowski, Chicago, IL (US); Cinda Sue Carlson, Oak Park, IL (US)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 960 days.

(21) Appl. No.: 10/764,114

(22) Filed: Jan. 23, 2004

(65) Prior Publication Data

US 2005/0164896 A1 Jul. 28, 2005

(51) Int. Cl.
*C11D 1/29* (2006.01)
*C11D 1/83* (2006.01)
*C11D 1/86* (2006.01)
*C11D 1/94* (2006.01)
*C11D 3/20* (2009.01)

(52) U.S. Cl. .............. 510/122; 510/124; 510/125; 510/128; 510/130; 510/137; 510/158; 510/159; 510/466; 510/473; 510/501; 510/506; 424/70.12; 424/70.21; 424/70.24; 424/70.31

(58) Field of Classification Search .......... 510/122, 510/124, 125, 128, 130, 137, 158, 159, 466, 510/473, 501, 506; 424/70.12, 70.21, 70.24, 424/70.31
See application file for complete search history.

(56) References Cited

U.S. PATENT DOCUMENTS

| | | | |
|---|---|---|---|
| RE34,584 E | | 4/1994 | Grote et al. |
| 6,165,454 A | * | 12/2000 | Patel et al. ............... 424/70.11 |
| 6,174,522 B1 | * | 1/2001 | Baravetto et al. ......... 424/70.12 |
| 6,489,286 B1 | | 12/2002 | Lukenbach et al. |
| 6,495,498 B2 | | 12/2002 | Niemiec et al. |
| 2002/0151446 A1 | * | 10/2002 | Piterski et al. .............. 510/130 |
| 2002/0173435 A1 | * | 11/2002 | Librizzi ...................... 510/130 |
| 2002/0192180 A1 | * | 12/2002 | Fairley et al. ............ 424/70.17 |
| 2003/0022799 A1 | * | 1/2003 | Alvarado et al. ............ 510/119 |
| 2003/0114323 A1 | * | 6/2003 | Booker et al. ............... 510/130 |
| 2005/0054547 A1 | * | 3/2005 | Ganopolsky et al. ........ 510/130 |

FOREIGN PATENT DOCUMENTS

| | | |
|---|---|---|
| DE | 196 11 558 | 9/1997 |
| EP | 0 485 212 | 5/1992 |
| EP | 0 839 513 | 5/1998 |
| EP | 1 352 644 | 10/2003 |
| FR | 2 774 900 | 8/1999 |
| WO | 99/13837 | 3/1999 |
| WO | WO99/53889 | * 10/1999 |
| WO | WO0002532 | * 1/2000 |

* cited by examiner

*Primary Examiner*—Gregory R Del Cotto
(74) *Attorney, Agent, or Firm*—Michael P. Aronson

(57) ABSTRACT

Mild shampoo compositions are described that are economical, have excellent in-use properties, and provide enhanced conditioning benefits. The compositions have low ocular irritation potential and are particularly suitable for use by children. The compositions include a surfactant system composed on an alkyl ethoxy sulfate having at least 3 ethylene oxide groups, a betaine surfactant, and an hydroxysultaine surfactant in specific ratios; and a non-volatile water-insoluble silicone. In-vitro tests are described that allows selection of optional ingredients that do not compromise the mildness or hair conditioning performance of the composition.

19 Claims, No Drawings

MILD, VISCOUS CLEANSING COMPOSITION WITH VERSATILE COMPATIBILITY AND ENHANCED CONDITIONING

BACKGROUND OF INVENTION

The present invention is directed at mild shampoo compositions that are economical, have excellent in-use properties, provide enhanced conditioning benefits. The compositions have low ocular irritation potential and are particularly suitable for use by children.

Mild or tear-free shampoos are well known in the art. Many have exceptional mildness and their tear-free benefits make them well suited to shampooing the hair of infants and very young children. However, traditional tear-free compositions do not lather particularly well nor do they provide effective hair conditioning and styling benefits.

There is a growing popularity among older children and teenagers for gentle, tear-free shampoos that are designed for them but provide the copious lather and conditioning/detangling benefits delivered by adult shampoos. This has become especially important in view of recent fashion trends towards longer hair and the wide spread use of blow-drying.

A second problem encountered with traditional tear-free shampoos concerns economy in use. Children and teenagers tend to shampoo their hair more frequently than adults do. Furthermore, because these compositions do not foam particularly well and are frequently thin, they tend to be overdosed to achieve a reasonable level of foam. Consequently, traditional tear-free shampoos are not perceived to be effective and economical (especially by parents) which tends to limit their use to infants and very small children.

One objective of the present invention is a mild, tear-free shampoo composition that has excellent in-use properties especially rich voluminous foam.

Another objective is a mild, tear-free shampoo composition that provides hair conditioning and detangling benefits even after blow-drying.

A still further objective is a mild, tear-free composition that combines excellent in-use properties with effective hair conditioning/detangling benefits yet is both thick and efficient so that it is economical for use by children and teenagers.

These and other objectives will become clear from the description of the invention.

The following patents and publications have been considered:

U.S. Pat. No. 6,489,286 describes compositions including surfactants, two cationic conditioning polymers and a volatile silicone.

U.S. Pat. No. 6,495,498 describes compositions including water-soluble silicones, a cationic conditioning agent and a detergent.

U.S. Re. 34,584 describes compositions including a surfactant, an insoluble, non-volatile silicone, a suspending agent and water. The suspending agents are long-chain acyl derivative or long-chain amine oxide.

None of the references cited above teaches the specific combination of ingredients at the critical ratios disclosed herein.

SUMMARY OF THE INVENTION

The subject invention provides a mild, tear-free shampoo composition which is economical and has excellent lather, conditioning properties by combining specific anionic and amphoteric surfactants in well defined ratios, specific conditioning agents, and optionally compatible cationic polymers and highly efficient thickening/suspending agents.

More specifically, the mild aqueous shampoo composition comprises the following ingredients in the amounts and ratios indicated:

i) an alkyl ethoxy sulfate wherein the alkyl group has an average of 12-16 carbon atoms and a degree of ethoxylation of at least 3,
ii) from about 2% to about 7% of an betaine surfactant,
iii) from about 2% to about 7% of an hydroxysultaine surfactant,
iv) from about 0.1% to about 5% of a non-volatile, water-insoluble silicone,
v) at least about 70 wt % water;

wherein the weight ratio of the betaine surfactant to the hydroxysultaine surfactant is in the range of from about 0.5 to about 1.5, and the weight ratio of the alkyl ethoxy sulfate to the sum of the weights of betaine surfactant and hydroxysultaine surfactant is in the range of from about 0.5 to about 1.5.

DETAILED DESCRIPTION OF THE INVENTION

As used herein % or wt % refers to percent by weight of an ingredient as compared to the total weight of the composition or component that is being discussed.

The present invention relates to shampoo and conditioning compositions that include a mild, tear-free and efficient surfactant system, a non-volatile, water-insoluble silicone, and an optional thought desirable cationic polymer and efficient thickening system. These components are discussed in detail below.

Surfactant System

The surfactant system is composed of the combination of three essential surfactants: one is an anionic surfactant and two are amphoteric surfactants.

The anionic surfactant is an alkyl ethoxy sulfate having the general formula

$$R\text{—}(O\text{—}CH_2\text{—}CH_2\text{—})_x\text{—}OSO_3M$$

wherein R is an alkyl group having a straight or branched alkyl chain. The alkyl group can contain 8-20 carbon atoms, preferably 10-18 carbon atoms and most preferably 12-15 carbon atoms. "X" represents the average ethylene oxide content per surfactant molecule and can in principle be in the range from about 1 and about 10. However to achieve adequate mildness (i.e., low ocular irritation potential), X should be preferably at least 3 and most preferably between about 3 and about 3.5 as this ethylene oxide content yields compositions having adequate mildness without compromising foam performance.

"M" represents a cation, preferably a monovalent cation, and most preferably a sodium, an ammonium or an alkanolammonium ion.

The alkyl ethoxy sulfate can be present is the composition in an amount ranging from about 4% to about 15%, preferably 5% to about 10%, and most preferably 6% to 8% based on the total weight of the composition. Higher levels of ethoxysulfate can be accommodated at a given betaine/hydroxysultaine ratio without compromising ocular irritation as the degree of ethoxylation increases.

The second essential component of the surfactant system is a mixture of amphoteric surfactants including a betaine component and a hydroxysultaine component.

The betaine component is defined by the following structure:

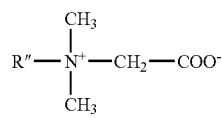

where R" is either an alkyl or an alkyl amidoakyl group. The alkyl group in either case can be branched or straight chain alkyl group having 8-18 carbon atoms, preferably 10-16 carbon atoms and most preferably 10-14 carbon atoms. Available betaines include oleyl betaine, caprylamidopropyl betaine, lauramidopropyl betaine, isostearylamidopropyl betaine, coco imidoazolinium betaine.

Particularly preferred betaines are lauryl or coco betaine, and lauryl or coco amidopropyl betaine.

The third essential component of the surfactant system is an hydroxysultaine (CTFA name for a sulfobetaine having the hydroxypropyl sulfonate group) which are generally formed from the reaction of a tertiary amine with epichlorohydrin and a bisulfite. Their general structure is:

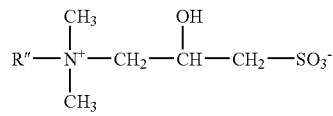

where R" is either an alkyl or an alkyl amidoalkyl group. The alkyl group in either case can be branched or straight chain alkyl group having 8-18 carbon atoms, preferably 10-16 carbon atoms and most preferably 10-14 carbon atoms. Commercially available sultaines include: lauryl hydroxy sultaine, tallowamidopropyl hydroxy sultaine, erucamidopropyl hydroxy sultaine, and alkylether hydroxypropyl sultaine.

Particularly preferred hydroxysultaines are coco and lauryl propylhydroxy sultaine and coco amidopropyl hydroxysultaine.

The weight ratio of betaine to hydroxysultaine and the relative proportions of the ethoxysulfate to total amphoteric (betaine plus hydroxysultaine) are critical to achieve wide formulation compatibility and a high degree of mildness. The weight ratio of betaine to hydroxysultaine should be in the range from about 0.5 to about 1.5, preferably from about 0.6 to about 1.0, and most preferably from about 0.7 to about 0.85. The weight ratio of ethoxysulfate to total amphoteric should be in the range from about 0.5 to about 1.5, preferably from about 0.8 to about 1.2, and most preferably from about 0.9 to about 1.1

Certain optional surfactants can be incorporated at low levels in the composition so long as they do not compromise the mildness of the composition especially its ocular irritation potential and hair conditioning performance. This can be assessed via the in-vitro tests described in the METHODOLOGY SECTION (see Florescein Leakage Assay and Wet and Dry Combing Force Assay). Examples of acceptable optional surfactants that can be used at low levels, typically under 3% and preferably under 2% are ethoxylated alkyl sulfosuccinates, alcohol ethoxylates having greater that 7 ethylene oxide groups, alkyamphodiacetates, alkylamphodipropionates, alkyliminodipropionates, alkyl sacrosinate, alkyl ethoxy carboxylates, ethoxylated sorbitan monoesters of fatty acids, polyoxyethylene derivatives of polyol esters.

Certain surfactants, however, should be minimized. These include alkyl sulfates and alkyl or alkyl aryl sulfonates, ethoxylated alkylphenols, ethanolamides of aliphatic acids. If required these surfactants should be used at a level less than 2%, preferably less than 1.5% and most preferably less than 1% by weight of the total composition.

Non-Volatile, Water-Insoluble Silicone

The shampoo compositions of the present invention further comprise a silicone hair-conditioning agent at concentrations effective to provide hair conditioning benefits. Such concentrations range from about 0.01% to about 5%, preferably from about 0.1% to about 5%, and most preferably from about 0.2% to about 3%, by weight of the shampoo compositions.

The silicone hair conditioning agents of the invention are insoluble in water and in the shampoo compositions, and are nonvolatile. Typically it will be intermixed in the shampoo composition so as to be in the form of a separate, discontinuous phase of dispersed, insoluble particles, also referred to as droplets. These droplets are typically suspended with an optional suspending agent described hereinafter. The silicone hair conditioning agent phase will comprise a silicone fluid hair conditioning agent such as a silicone fluid and can also comprise other ingredients, such as a silicone resin to improve silicone fluid deposition efficiency or enhance glossiness of the hair (especially when high refractive index (e.g. above about 1.46) silicone conditioning agents are used (e.g. highly phenylated silicones).

The silicone hair conditioning agents for use in the shampoo compositions preferably have a viscosity of from about 20 to about 2,000,000 centistokes, more preferably from about 1,000 to about 1,800,000 centistokes, even more preferably from about 50,000 to about 1,500,000 most preferably from about 100,000 to about 500,000 centistokes, as measured at 25. degree. C.

Silicone fluids include silicone oils which are flowable silicone materials having a viscosity of less than 1,000,000 centistokes, preferably between about 5 and 1,000,000 centistokes, more preferably between about 10 and about 100,000 centistokes, at 25. degree. C. Suitable silicone oils include polyalkyl siloxanes, polyaryl siloxanes, polyalkylaryl siloxanes, polyether siloxane copolymers, and combinations thereof. Other insoluble, nonvolatile silicone fluids having hair conditioning properties can also be used.

Viscosity can be measured by means of a glass capillary viscometer as set out further in Dow Corning Corporate Test Method CTM004 Jul. 20 1970. The average silicone particle size of the emulsified silicone in the shampoo composition is suitably less than 20 microns, preferably less than 10 microns. Ideally it ranges from 0.15 to 2 microns, optimally from 0.2 to 1 micron.

Silicone oils include polyalkyl or polyaryl siloxanes containing substituent groups that include alkoxy, aryloxy, alkaryl, arylalkyl, arylalkenyl, alkamno, and ether-substituted, hydroxyl-substituted, and halogen-substituted aliphatic and aryl groups. The substituent groups can also include cationic amines and quaternary ammonium groups.

The aliphatic or aryl groups substituted on the siloxane chain may have any structure so long as the resulting silicones remain fluid at room temperature, are hydrophobic, are neither irritating, toxic nor otherwise harmful when applied to the hair, are compatible with the other components of the shampoo compositions, are chemically stable under normal use and storage conditions, are insoluble in the shampoo compositions herein, and are capable of being deposited on and conditioning the hair.

Preferred alkyl and alkenyl substituents are $C_1$-$C_5$ alkyls and alkenyls, more preferably from $C_1$-$C_4$, most preferably from $C_1$-$C_2$. The aliphatic portions of other alkyl-, alkenyl-, or alkynyl-containing groups (such as alkoxy, alkaryl, and alkamino) can be straight or branched chains and preferably have from one to five carbon atoms, more preferably from one to four carbon atoms, even more preferably from one to three carbon atoms, most preferably from one to two carbon atoms. As discussed above, the substituents can also contain amino functionality, e.g. amino groups, which can be primary, secondary or tertiary amines or quaternary ammonium. These include mono-, di- and tri-alkylamino and alkoxyamino groups wherein the aliphatic portion chain length is preferably as described above.

Suitable substituent groups on the siloxane chain include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred. Other suitable groups include methyl, methoxy, ethoxy, propoxy, and aryloxy. The three R groups on the end caps of the silicone may also represent the same or different groups.

The nonvolatile polyalkylsiloxane fluids that may be used include, for example, polydimethylsiloxanes. These siloxanes are available, for example, from the General Electric Company in their Viscasil R and SF 96 series, and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide concentrations must be sufficiently low to prevent solubility in water and in the composition hereof.

Suitable alkylamino substituted silicones include those known by the CTFA designation "amodimethicone". An especially preferred cationic polymer is known as "trimethylsilylamodimethicone".

Other silicone fluids are the insoluble silicone gums. These gums are polyorganosilxane materials having a viscosity at 25. degree. C. of greater than or equal to 1,000,000 centistokes. Silicone gums are described in U.S. Pat. No. 4,152, 416; Noll and Walter, Chemistry and Technology of Silicones, New York: Academic Press 1968; and in General Electric Silicone Rubber Product Data Sheets SE 30, SE 33, SE 54 and SE 76, all of which are incorporated herein by reference. The silicone gums will typically have a mass molecule weight in excess of about 200,000, generally between about 200,000 and about 1,000,000, specific examples of which include polydimethylsiloxane, (polydimethylsiloxane)(methylvinylsiloxane) copolymer, poly(dimethylsiloxane)(diphenyl siloxane)(methylvinylsiloxane) copolymer and mixtures thereof.

Another category of nonvolatile, insoluble silicone fluid conditioning agents are the high refractive index silicones, having a refractive index of at least about 1.46, preferably at least about 1.48, more preferably at least about 1.52, most preferably at least about 1.55. The refractive index of the polysiloxane fluid will generally be less than about 1.70, typically less than about 1.60. In this context, polysiloxane "fluid" includes oils as well as gums. The high refractive index polysiloxane fluids contain a sufficient amount of aryl-containing substituents to increase the refractive index to the desired level, which is described above.

Aryl-containing substituents contain alicyclic and heterocyclic five and six membered aryl rings, and substituents containing fused five or six membered rings. The aryl rings themselves can be substituted or unsubstituted. Substituents include aliphatic substituents, and can also include alkoxy substituents, acyl substituents, ketones, halogens (e.g., Cl and Br), amines, etc. Exemplary aryl-containing groups include substituted and unsubstituted arenes, such as phenyl, and phenyl derivatives such as phenyls with $C_1$-$C_5$ alkyl or alkenyl substituents, e.g., allylphenyl, methyl phenyl and ethyl phenyl, vinyl phenyls such as styrenyl, and phenyl alkynes (e.g. phenyl $C_2$-$C_4$ alkynes). Heterocyclic aryl groups include substituents derived from furan, imidazole, pyrrole, pyridine, etc. Fused aryl ring substituents include, for example, naphthalene, coumarin, and purine.

In general, the high refractive index polysiloxane fluids will have a degree of aryl-containing substituents of at least about 15%, preferably at least about 20%, more preferably at least about 25%, even more preferably at least about 35%, most preferably at least about 50%. Typically, although it is not intended to necessarily limit the invention, the degree of aryl substitution will be less than about 90%, more generally less than about 85%, preferably from about 55% to about 80%.

The polysiloxane fluids are also characterized by relatively high surface tensions as a result of their aryl substitution. In general, the polysiloxane fluids hereof will have a surface tension of at least about 24 dynes/cm.sup.2, typically at least about 27 dynes/cm.sup.2. Surface tension, for purposes hereof is measured by a de Nouy ring tensiometer according to Dow Corning Corporate Test Method CTM 0461, Nov. 23, 1971. Changes in surface tension can be measured according to the above test method or according to ASTM Method D 1331.

Preferred high refractive index polysiloxane fluids have a combination of phenyl or phenyl derivative substituents (preferably phenyl), with alkyl substituents, preferably C1-C4 alkyl (most preferably methyl), hydroxy, C1-C4 alkylamino. High refractive index polysiloxanes are available from Dow Corning Corporation (Midland, Mich., U.S.A.) Huls America (Piscataway, N.J., U.S.A.), and General Electric Silicones (Waterford, N.Y., U.S.A.).

It is preferred to utilize high refractive index silicones in solution with a spreading agent, such as a silicone resin or a surfactant, to reduce the surface tension by a sufficient amount to enhance spreading and thereby enhance glossiness (subsequent to drying) of hair treated with the composition. In general, a sufficient amount of the spreading agent to reduce the surface tension of the high refractive index polysiloxane fluid by at least about 5%, preferably at least about 10%, more preferably at least about 15%, even more preferably at least about 20%, most preferably at least about 25%. Reductions in surface tension of the polysiloxane fluid/spreading agent mixture can provide improved shine enhancement of the hair.

References disclosing examples of some suitable silicone fluids for use in the shampoo compositions include U.S. Pat. No. 2,826,551, U.S. Pat. No. 3,964,500, U.S. Pat. No. 4,364, 837, British Patent 849,433, and Silicon Compounds. Petrarch Systems, Inc. (1984), all of which are incorporated herein by reference.

Silicone resins can be included in the silicone conditioning agent. These resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and terachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Background material on silicones including sections discussing silicone fluids, gums, and resins, as well as manufacture of silicones, can be found in Encyclopedia of Polymer Science and Engineering, Volume 15, Second Edition, pp 204-308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g. M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbol indicating the total number of each type of unit in the silicone (or an average thereof) or as specifically indicated ratios in combination with molecular weight complete the description of the silicone material under the MDTQ system.

Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MDT and MDTD resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The weight ratio of the nonvolatile silicone fluid, having refractive index below 1.46, to the silicone resin component, when used, is preferably from about 4:1 to about 400:1, preferably this ratio is from about 9:1 to about 200:1, more preferably from about 19:1 to about 100:1, particularly when the silicone fluid component is a polydimethyl-siloxane fluid or a mixture of polydimethylsiloxane fluid and polydimethylsiloxane gum as described above. Insofar as the silicone resin forms a part of the same phase in the compositions hereof as the silicone fluid, i.e. the conditioning active, the sum of the fluid and resin should be included in determining the level of silicone conditioning agent in the composition.

The silicone component can consist of droplets that are in the normal emulsion size range or it can comprise a microemulsion consisting of droplets less than about 0.1 micron. Microemulsified silicones are especially suitable for use in clear shampoo compositions. Further the silicone component can consist of a blend of emulsified particles of insoluble silicone of specified average silicone particle size and microemulsified particles of insoluble silicone of specified average silicone particle size.

The silicones are insoluble in the aqueous matrix of the shampoo composition and so are present in emulsified and/or microemulsified forms respectively, with the silicones present as dispersed particles. Particle size may be measured by means of a laser light scattering technique, using a 2600D Particle Sizer from Malvern Instruments. The measure of average particle size using this technique is the "D5011 value.

In addition to polydiorganosiloxanes and aminofunctional silicones, the polydiorganosiloxanes can have hydroxyl end groups, which have the CTFA designation dimethiconol.

In the case of mixtures, the emulsified particles of insoluble silicone may be of the same silicone type as the microemulsified particles of insoluble silicone, or may be different. Suitable silicone emulsions and microemulsions for use in the invention are commercially available in a pre-emulsified form. Such pre-formed emulsions can then be incorporated into the shampoo composition by simple mixing, which is particularly advantageous for ease of processing. Pre-formed emulsions are available from suppliers of silicone oils such as Dow Corning, General Electric, Union Carbide, Wacker Chemie, Shin Etsu, Toshiba, Toyo Beauty Co, and Toray Silicone Co.

An aqueous emulsion is the preferred form for such a pre-formed emulsion. In such emulsions, it is usual that the emulsion additionally includes at least one emulsifier in order to stabilize the silicone emulsion. Suitable emulsifiers are well known in the art and include anionic and nonionic surfactants. Examples of anionic surfactants used as emulsifiers for the silicone particles are alkylarylsulphonates, e.g., sodium dodecylbenzene sulphonate, alkyl sulphates e.g., sodium lauryl sulphate, alkyl ether sulphates, e.g., sodium lauryl ether sulphate nEO, where n is from 1 to 20 alkylphenol ether sulphates, e.g., octylphenol ether sulphate nEO where n is from 1 to 20, and sulphosuccinates, e.g., sodium dioctylsulphosuccinate.

Examples of nonionic surfactants used as emulsifiers for the silicone particles are alkylphenol ethoxylates, e.g., nonylphenol ethoxylate nEO, where n is from 1 to 50, alcohol ethoxylates, e.g., lauryl alcohol nEO, where n is from 1 to 50, ester ethoxylates, e.g., polyoxyethylene monostearate where the number of oxyethylene units is from 1 to 30.

Examples of suitable pre-formed emulsions include emulsions DC2-1766, DC2-1784, and DC2-1310, all available from Dow Corning. These are all emulsions of dimethiconol. DC2-1766 and DC2-1784 each have an average silicone particle size in the emulsion of less than 2 microns. DC2-1310 has an average silicone particle size in the emulsion of about 8 microns. Cross-linked silicone gums are also available in a pre-emulsified form. A preferred example is the material available from Dow Corning as DC X2-1787, which is an emulsion of cross-linked dimethiconol gum having an average silicone particle size in the emulsion of about 0.5 microns.

The average silicone particle size of the microemulsified silicone in the shampoo composition is suitably less than less than 0.075 micron. Ideally it ranges from 0.01 to 0.075 micron, optimally from 0.02 to 0.05 micron.

Examples of suitable pre-formed microemulsions include microemulsions DC2-1865 and DC2-1870, available from Dow Corning. These are microemulsions of dimethiconol. DC2-1865 and DC2-1870 each have an average silicone particle size in the microemulsion of less than 0.075 microns. Cross-linked silicone gums are also available in a pre-microemulsified form, which is advantageous for ease of formulation. A preferred example is the material available from Dow Corning as DC X2-1391, which is a microemulsion of cross-linked dimethiconol gum having an average silicone particle size in the microemulsion of about 0.045 microns.

It has been reported in WO9953889 that the conditioning performance of silicone in a surfactant-based shampoo composition can be significantly boosted by utilizing a combination of emulsified silicone and microemulsified silicone, in the shampoo composition. The weight ratio of emulsified particles of silicone to microemulsified particles of silicone suitably ranges from 4:1 to 1:4. Preferably, the ratio of emulsified particles of silicone to microemulsified particles of silicone ranges from 3:1 to 1:3, more preferably from 2:1 to 1:1.

Optional Ingredients

Cationic polymer: Cationic polymers are optionally employed to provide enhanced deposition of the non-volatile, water-insoluble silicone as well as conditioning benefits in their own right.

The cationic conditioning polymer contains cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the shampoo composition. The average molecular weight of the cationic conditioning polymers is between about 10 million and about 5,000, preferably at least about 100,000, more preferably at least about 200,000, but preferably not more than about 2 million, preferably not more than about 1.5 million. The polymers also have a cationic charge density ranging from about 0.2 meq/gm to about 7 meq/gm, preferably at least about 0.4 meq/gm, more preferably at least about 0.6 meq/gm, but also preferably less than about 5 meq/gm, more preferably less than about 2 meq/gm, at the pH of intended use of the shampoo composition, which pH will generally range from about pH 3 to about pH 9, preferably between about pH 5 and about pH 8.

Any anionic counterions can be use in association with the cationic conditioning polymers so long as the polymers remain soluble in water, in the shampoo composition, or in a coascervate phase of the shampoo composition, and so long as the counterions are physically and chemically compatible with the essential components of the shampoo composition or do not otherwise unduly impair product performance, stability or aesthetics.

Non limiting examples of such counterions include halides (e.g., chlorine, fluorine, bromine, iodine), sulfate and methylsulfate.

The cationic nitrogen-containing moiety of the cationic polymer is generally present as a substituent on all, or more typically on some, of the monomer units thereof. Thus, the cationic polymer for use in the shampoo composition includes homopolymers, copolymers, terpolymers, and so forth, of quaternary ammonium or cationic amine-substituted monomer units, optionally in combination with non-cationic monomers referred to herein as spacer monomers. Non-limiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982), which description is incorporated herein by reference.

Particularly suitable cationic polymers for use in the shampoo composition include polysaccharide polymers, such as cationic cellulose derivatives and cationic starch derivatives. Suitable cationic polysaccharide polymers include those which conform to the formula

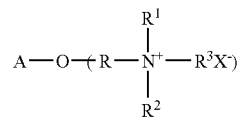

wherein A is an anhydroglucose residual group, such as a starch or cellulose anhydroglucose residual; R is an alkylene oxyalkylene, polyoxyalkylene, or hydroxyalkylene group, or combination thereof, R1, R2, and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) preferably being about 20 or less; and X is an anionic counterion as described in hereinbefore.

Especially preferred cationic conditioning polymers are the cationic cellulose polymers especially like those polymers available from Amerchol Corp. (Edison, N.J.,) in their Polymer JR and LR series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted opoxide, referred to in the industry (CIFA) as Polyquaternium 24. These materials are available from Amerchol Corp. (Edison, N.J.,) under the trade name Polymer LM-200. The level of cationic cellulose in the composition can be in the range from about 0.01 to about 2%, preferably from about 0.1 to about 0.6%, and most preferably from about 0.15 to about 0.45%.

Although cationic cellulose polymers are preferred other types of cationic polymers may be incorporated at low levels as optional additives provided they do not interfere with stability. Examples of such optional cationic polymers include either modified natural polymers or synthetic polymers. The level of these optional polymers should preferably be incorporated in the range of about 10% to about 25% based on the weight of the cationic cellulose present in the formulation.

Suitable optional modified natural polymers include cationic guar gum derivatives, such as guar hydroxypropyltrimonium chloride, specific examples of which include the Jaguar series commercially available from Celanese Corporation. Other suitable cationic polymers include quaternary nitrogen-containing cellulose ethers, some examples of which are described in U.S. Pat. No. 3,962,418, which description is incorporated herein by reference herein. Other suitable cationic polymers include copolymers of etherified cellulose, guar and starch, some examples of which are described in U.S. Pat. No. 3,958,581, which description is incorporated herein by reference.

Non limiting examples of suitable optional synthetic cationic polymers include copolymers of vinyl monomers having cationic protonated amine or quaternary ammonium functionality with water soluble spacer monomers such as acrylamide, methacrylamide, alkyl and dialkyl acrylamides, alkyl and dialkyl methacrylamides, alkyl acrylate, allyl methacrylate, vinyl caprolactone or vinyl pyrrolidone. The alkyl and dialkyl substituted monomers preferably have from $C_1$ to $C_7$ alkyl groups, more preferably from $C_1$ to $C_3$ alkyl groups. Other suitable spacer monomers include vinyl esters, vinyl alcohol (made by hydrolysis of polyvinyl acetate), maleic anhydride, propylene glycol, and ethylene glycol.

Other suitable optional synthetic polymers include protonated amino and quaternary ammonium monomers, for inclusion in the cationic polymers of the shampoo composition herein, include vinyl compounds substituted with dialkylaminoalkyl acrylate, dialkylaminoalkyl methacrylate, monoalaylaminoalkyl acrylate, monoalkylaminoalkyl methacrylate, trialkyl methacryloxyalkyl ammonium salt, trialkyl acryloyalyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$, $C_2$ or $C_3$ alkyls.

Other suitable optional synthetic polymers include amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$-$C_7$ hydrocarbyls, more preferably $C_1$-$C_3$ alkyls.

Still other suitable optional synthetic polymers for use in the shampoo composition include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., U.S.A) under the LUVIQUAT tradename (e.g., LUVIQUAT FC 370); copolymers of 1-vinyl-2-pyrrolidone and dimethylaminoethyl methacrylate (refereed to in the industry by CTFA as Polyquaternium-11) such as those commercially available from ISP Corporation (Wayne, N.J., U.S.A.) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homopolymers and copolymers of unsaturated carboxylic acids having from 3 to 5 carbon atoms, as described in U.S. Pat. No. 4,009,256, which description is incorporated herein by reference.

Thickening and suspending agents: The compositions of the present invention preferably further comprise thickening/suspending agents to ensure that insoluble materials are stable. A variety of materials can be employed. These include swelling and associative polymers, finely divided crystalline or amorphous inorganic and organic materials that form networks, electrolytes and combinations thereof.

Organic polymers include carboxyvinyl polymers such as the copolymers of acrylic acid crosslinked with polyallylsucrose as described in U.S. Pat. No. 2,798,053, which description is incorporated herein by reference. Examples of these polymers include Carbopol 934, 940, 941, and 956, available from B. F. Goodrich Company and the alkali swellable acrylic latex polymers sold by Rohm and Haas under the ARYSOL or ACULYN trade names.

Other suitable suspending agents include xanthan gum at concentrations ranging from about 0.3% to about 3%, preferably from about 0.4% to about 1.2%, by weight of the shampoo compositions. The use of xanthan gum as a suspending agent in silicone containing shampoo compositions is described, for example, in U.S. Pat. No. 4,788,006, which description is incorporated herein by reference. Combinations of long chain acyl derivatives and xanthan gum may also be used as a suspending agent in the shampoo compositions. Such combinations are described in U.S. Pat. No. 4,704,272, which description is incorporated herein by reference.

Other suitable polymeric suspending agents may be used in the shampoo compositions, including those that can impart a gel-like viscosity to the composition, such as water soluble or colloidally water soluble polymers like cellulose ethers (e.g., methylcellulose, hydroxybutyl methylcellulose, hydropylcellulose, hydroxypropyl methylcellulose, hydroxyethyl ethylcellulose and hydorxethylcellulose), guar gum, polyvinyl alcohol, polyvinyl pyrrolidone, hydroxypropyl guar gum, starch and starch derivatives, and other thickeners, viscosity modifiers, gelling agents, etc. Mixtures of these materials can also be used.

Optional crystalline organic suspending agents include acyl derivatives, long chain amine oxides, or combinations thereof, concentrations of which range from about 0.1% to about 5.0%, preferably from about 0.5% to about 3.0%, by weight of the shampoo compositions. When used in the shampoo compositions, these suspending agents are present in crystalline form. These suspending agents are described in U.S. Pat. No. 4,741,855, which description is incorporated herein by reference. These suspending agents include ethylene glycol esters of fatty acids preferably having from about 16 to about 22 carbon atoms. Examples include ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having $C_8$-$C_{22}$ chains may be used.

Examples of suitable long chain amine oxides for use as suspending agents include alkyl ($C_{16}$-$C_{22}$) dimethyl amine oxides, e.g., stearyl dimethyl amine oxide.

Another useful crystalline suspending agent is trihydroxystearin sold under the trade name THIXCIN®.

Network forming inorganic materials include but are not limited to clays, and silicas. Examples of clays include smectite clay selected from the group consisting of bentonite and hectorite and mixtures thereof. Synthetic hectorite (laponite) clay are often used with an electrolyte salt capable of causing the clay to thicken (alkali and alkaline earth salts such as halides, ammonium salts and sulfates). Bentonite is a colloidal aluminum clay sulfate. Examples of silica include amorphous silica and include fumed silica and precipitated silica and mixtures thereof.

Associative polymers are those which incorporate hydrophobic groups which can form labile crosslinks alone or with the participation of surfactant micelles. An example of associative polymers the hydrophobically modified cross linked polyacrylates sold by Noveon under the PEMULEN trade name. Other example are the hydrophobically modified cellulose ethers and hydrophobically modified polyurethanes.

A particularly preferred class of thickening and suspending agent in the present invention are hydrophobically modified water-soluble nonionic polyols. Suitable hydrophobically modified water-soluble nonionic polyols for use herein are PEG 120 methyl glucoside dioleate (available from Amercol under the trade name GLUCAMATE DOE 120), PEG-150 pentaerythrityl tetrastearate (available from Croda under the trade name CROTHIX, PEG-75 dioleate (available from Kessco under the trade name PEG-4000 DIOLEATE and PEG-150 distearate (available from Witco under the trade name WITCONAL L32).

Long chain fatty esters of polyethylene glycol, e.g., PEG-150 distearate, are especially preferred thickening and suspending agents in the present invention. Although the PEG fatty esters can be used alone, it has been found that their effectiveness and efficiency can be greatly improved when they are combined with certain electrolytes. Especially preferred electrolytes for use in combination PEG-150 distearate, are sodium citrate and sodium chloride as they provide a synergistic thickening system that allows adequate thickening at low levels of inclusion in composition that have a low total concentration of surfactant, e.g., less than about 15 wt %. This is important in achieving mild tear-free formulations that provide excellent conditioning properties and are economical.

The above thickening and structuring agents can be used alone or in mixtures and may be present in an amount from about 0.1 wt % to about 10 wt % of the composition. When PEG-150 distearate/electrolyte mixtures are employed as the thickening system, the level of organic thickener can be substantially reduced to a level between about 0.1 to about 0.5 wt %, preferably between 0.2 wt % and 0.4 wt %.

Aesthetic and Adjunct Ingredients: A wide variety of optional ingredients can be incorporated in the formulation provided they do not interfere with the mildness and hair conditioning benefits provided by the composition. These include but are not limited to: perfumes, pearlizing and opacifying agents such as higher fatty alcohols, fatty acids, solid esters, nacreous "interference pigments" such as TiO2 coated micas, dyes and colorants, sensates such as menthol, preservatives including anti-oxidants and chelating agents, emulsion stabilizers, auxiliary thickeners, and mixtures thereof.

Additional hair and skin benefit agents: A variety of optional ingredients can be incorporated into the compositions of the instant invention to promote hair and scalp health. However, these ingredients should be chosen to be consistent with the tears-free mildness of the composition. Potential benefit agents include but are not limited to: lipids such as cholesterol, ceramides, and pseudoceramides, additional non-silicone hair conditioning agents such as synthetic hydrocarbon esters, humectants such as glycerol, antimicrobial agents such as zinc pyridinethione, sunscreens, and mixtures thereof.

Evaluation Methodology

Fluorescein Leakage In-Vitro Assay

The in-vitro model referred to as Fluorescein Leakage Assay is used to assess ocular irritation potential and is ideal for discriminating between or ranking the ocular mildness of products such as shampoo. The assay, which is known in the art, involves a monolayer cell culture which mimics the tight junctions found in the cornea of the eye. In this test, which is described below, the higher the leakage of sodium fluorescein through the cell culture, which is caused by a particular composition, the higher is the potential for ocular irritation to be caused by that composition.

The fluorescein leakage assay uses a cell culture system consisting of Madin-Darby Canine Kidney (MDCK) cells. As these cells proliferate, they form tight junctions analogous to those found in the outermost epithelium of human corneal tissue. The cells are grown on cell culture inserts until confluent and fed with nutrient media for a period of 7 days. Test material can then be applied neat or with varying degrees of dilution for a set length of time. The test material is rinsed off and 0.01% of sodium fluorescein applied for 30 minutes. The amount of sodium fluorescein that penetrates through the cell junctions is collected, measured and calculated as % permeability or leakage (amount of damage).

In addition, the cells can continue to be maintained for up to 5 days and the fluorescein re-applied daily to measure the degree of cell recovery.

The fluorescein Leakage In-vitro Assay was used to evaluate compositions of the invention as well as to compare their irritation potential with competitive benchmarks. In this assay a shampoo is typically tested in triplicate at a 5% dilution in water, applied topically to the MDCK monolayer for 30 seconds. The effect of the treatment is assessed as the % Permeability of sodium fluorescein through the monolayer after initial exposure and after a 24-hr recovery period. The results are expressed as the % permeability of fluorescein leakage through the cell layer.

Compositions of this invention should preferably have a % permeability of fluorescein leakage through the cell layer of less than about 10%, and more preferably less than about 8%. Compositions with this level of fluorescein leakage are classified as having minimal to mild ocular irritation potential.

Zein Solubility In-Vitro Assay

Zein solubility provides a simple directional indication of mildness and is widely used in the art for testing the mildness of both surfactant raw materials and shampoos. Zein is a protein (blends of amino acid derived from maize) which swells and denatures in response to surfactants in a similar way to skin keratin proteins. This procedure was developed on the basis that the more Zein solubilised by a given surfactant composition under standardized test conditions, the greater is the irritancy of the composition. Zein solubility is not intended as a replacement for clinical studies, or the more biologically based Fluorescein Leakage In-Vitro Assay even though a reasonable correlation has been demonstrated. Therefore the principle application for Zein solubility is for initial screening where it provides a good predictor of eventual irritation potential. Under the test conditions employed and described below a Zein solubility of less than 1% is a good indicator of potentially mild compositions while a Zein solubility greater than 1% is a good indication that the composition will irritating to eyes.

Apparatus

Analytical balance, 100 mL beakers, stir bars, medium stir plate, 10 mL syringe, 20 mL scintillation vials, conventional oven, set at 75° C.

Procedure
1. Weigh 6.25 g of shampoo into a 100-mL beaker and dilute it to 50 g with DI water.
2. Mix the solution on a stir plate @ 300 rpm (set dial at 4 on stirring plate) until the solution looks uniform or the entire sample is dissolved.
3. Record the pH of the solution.
4. Withdraw 6 mL of solution using a syringe.
5. Filter solution through a 0.45-micron syringe filter onto a scintillation vial.
6. Cap the vial and label it as blank. A blank is needed to correct for any soluble material.
7. Add 2 g of Zein to the remaining solution and equilibrate for 1 hour at constant stirring speed (300 rpm). After 10 minutes of stirring, if all or most of the Zein dissolved, add an additional 1 g of Zein. Keep adding more Zein in 1 g increments every 5-10 minutes until there is undissolved Zein floating in the solution.
8. After 1 hour of constant stirring, allow solution to settle for 5 minutes.
9. Withdraw 6 mL of the supernatant solution using a syringe and filter it through a 0.45 micron syringe filter onto a scintillation vial.
10. Cap the vial and label it as sample.
11. Perform nonvolatiles on both samples using a conventional oven set at 75° C. Allow samples to dry overnight.
12. Calculate the percent Zein dissolved.

Calculation

% Zein solubilised=% nonvolatile of sample−% non-volatile of blank

Wet and Dry Combing Force in-vitro Assay

As shown in the paper by Garcia and Dias (*Combability measurements on human hair*, J Soc. Cosmet. Chem., Vol 27 379-398 (1976)), incorporated by reference herein, the ease of combing can be measured instrumentally by monitoring the frictional forces which result as the hair passes through a comb. These combing forces are measured as a function of the distance traveled along the tress. Parameters such as the maximum combing force, the average combing force and/or the combing energy can then be used to evaluate performance. Product distinctions are easier to detect during wet combing experiments. The procedure listed below specifically relates to wet combing experiments, with a later section outlining method modifications which are used for dry combing.

Apparatus

Tensile Testing equipment (preferably an Instron equipped with a 500 g load cell, or alternatively a Diastron Mini-Tensile Tester), standard 2 g tresses, hard rubber combs and an "intellifaucet".

Procedure

Tress Preparation: Tresses are first washed thoroughly. Eight standard 2 g tresses are used in the evaluation of each product. The sensitivity of combing experiments can be significantly improved through the use of damaged hair tresses. Bleached tresses can be used in the evaluation of conditioning effects from shampoo compositions.

Sample Application: 0.2 mL of product is applied to a 2 g tress. The product is left in contact with the hair for 1 minute. At the end of this time, the tress is rinsed for 30 seconds using standard tap water at 40° C. and a flow rate of 2 L/min.

Instrumental Conditions: The treated tresses are manually pre-combed to remove any large tangles/snags within the hair. The tresses are then mounted in the instrument and combed at a speed of 40 inches/min. Seven combing curves are measured per tress. The first combing stroke is often significantly higher than the others as it still contains a considerable contribution from detangling. For this reason, the first combing curve is discarded. Any other combing curves which contain unusually high spikes as a result of knots, snags, etc. are also omitted.

Calculations: From these combing curves it is then possible to extract parameters such as the maximum combing force, the average combing force and/or the combing energy. The maximum combing force is the highest load recorded during the experiment, the average energy is an averaged value between two pre-determined points, while the combing energy is the energy under the curve. When using the Instron 5500, experimental conditions and generation of the calculated parameters can be obtained automatically by using the pre-set "COMBING2" method.

Statistical Analysis of Data: Data is analyzed by the Tukey HSD test at the 95% confidence limit.

Modifications to Procedure for Dry Combing: For dry combing, the treated tresses are allowed to air dry and are conditioned overnight at 60% relative humidity. Dry combing experiments are carried out in the same manner as outlined above, except that the humidity during the experiment is also regulated at 60%.

Silicone Retention In-Vitro Assay

Silicone polymers, such as dimethicone and some amino functional silicones, can be extracted from tresses treated with hair care formulations using organic solvents. Tresses treated with crosslinked or reactive silicone resins may require chemical treatment, such as aminolysis with anhydrous amines, before extraction of silicone is possible. Hexane is a good extractant for most silicone polymers from hair. However, if a single extraction of the tress is to be used as sample preparation for a number of analyses, including the measurement of ionic surfactants by mass spectrometry, chloroform is the solvent of choice.

A weighed amount of hair is extracted twice with organic solvent using an ultrasonic bath to aid the extraction. The extracts are combined, concentrated, and analyzed for silicon using an Inductively Coupled Plasma (ICP) spectrometer that has been standardized with a solution containing dimethicone, for which the silicon fraction is known.

Apparatus: Inductively Coupled Plasma Atomic Emission Spectrometer (ICP-AES); wide-mouth jars, 8 oz; scissors; balance—analytical, accurate to ±0.01 g; ultrasonic bath; graduated cylinder—50 mL, pipette—class A, TD, 10 mL Reagents: Hexane—spectrophotometric grade, Chloroform—spectrophotometric is grade, dimethicone—a siloxane polymer that contains 37.9 weight percent silicon Procedure Extraction of tresses: Two 2 g hair tresses that were treated with the same test shampoo composition were cut into pieces about 1.5 inches long. These cut samples are mixed to make a composite sample and 1.0 to 1.25 g of each is weighted into an 8 oz jar. 50 mL of organic solvent is added to each jar and swirled to wet the hair. The jars are then Capped tightly and placed in an ultrasonic bath for 30 minutes. The solvent is then decanted into a clean jar and the solvent is allowed to evaporate in a hood. To perform a second duplicate extraction, 50 mL of organic solvent are added to the hair in the original jar, cap, and again place in an ultrasonic bath for 30 minutes.

This second sample is decanted into the jar containing the residue from the first extract and again allowed to evaporate in the hood.

Preparation of Samples and Standard: The residue from the combined extracts is dissolved in 10 mL chloroform using sonication to aid in the removal of all the residue from the jar surfaces. A calibration standard solution is prepared by dissolving dimethicone in chloroform, so that the concentration of silicon is at a level slightly higher than that expected in the sample.

Spectrophotometric Measurement: A 1.0 mm center tube is installed in the ICP torch, which is used for analyzing samples in organic solvent and the 251.6 nm line is selected for analysis of silicon. The instrument is standardized by sequentially aspirating a chloroform blank and then the dimethicone standard. The samples are then aspirated and the value for silicon concentration recorded.

Calculation: Micrograms (μg) silicone per gram of hair is calculated from the following equation:

$$\mu g \text{ silicon/g hair} = \frac{\frac{\mu g \text{ silicon}}{mL \text{ sample solution}} (10 \text{ mL sample solution})}{g \text{ hair}}$$

To convert μg silicon to silicone polymer as dimethicone: dimethicone contains 37.9 weight percent silicon.

$$\mu g \text{ dimethicone/g hair} = \frac{\mu g \text{ silicon/g hair}}{\frac{37.9}{100}}$$

Ease of Wet-Combing Rank Order In-Vitro Panel Test

This test is a forced choice comparative ranking of the ease of combing provided by a given set of shampoo compositions under in-vitro conditions that are representative of normal use. The test utilizes human evaluation of ease of combing of hair tresses that have been treated with test and control compositions using a forced choice ranking system. The test provides a good indication of the comparative level of detangling benefits provided by a composition relative to well defined control compositions or no composition (untreated).

Procedure

Tress Preparation: Tresses are first washed thoroughly. Standard 2 g tresses are used in the evaluation of each product. The sensitivity of combing experiments can be significantly improved through the use of damaged hair tresses. Bleached tresses can be used in the evaluation of conditioning effects from shampoo compositions.

Sample Application: 0.2 mL of product is applied to a 2 g tress. The product is worked into the hair with twenty strokes over 20 seconds. At the end of this time, the tress is rinsed for 30 seconds using standard tap water at 40° C. and a flow rate of 2 L/min.

Combing Evaluations: The treated and still damp tresses are pre-combed to remove any large tangles/snags within the hair. A tress treated with each product under evaluation is blind-labeled and suspended on a rack to create a set for comparison. One tress in the set is left untreated. Multiple combing panels comparing a set of treatments can be prepared with the order of treatments randomized from panel to panel. Within each panel an individual then combs each tress and ranks its ease of combing. For example, in a panel containing four tresses, the subject would rank the tress displaying easiest combing a value of 1, while the tress displaying most difficult combing would be given a value of 4. Multiple evaluators comb and rank the tresses within each panel and their ranking results are then tabulated.

Statistical Analysis of Data: Data is analyzed by the Tukey HSD test at the confidence limits of 90% and 95%.

In-Vitro Assays as Means of Evaluating Optional Ingredients

The Fluorescein leakage, Zein Solubility, Wet-Combing, and Silicone Deposition Assays described above are also very useful in assessing the potential impact of optional ingredients on the performance of the composition and thus screening whether optional ingredients are suitable for inclusion.

For example, as will be shown in the examples below, a highly effective composition that combines high mildness (low ocular irritation potential) and excellent conditioning performance consists essentially of the surfactants alkyl ethoxy ether sulfate ($\geq 3EO$), betaine, and hydroxysultaine in the ratios specified herein; a cationic cellulose polymer; a non-volatile, water-insoluble silicone; PEG-150 distearate; and an electrolyte such sodium chloride. Numerous aesthetic and shampoo adjuncts and optional ingredients can be included at low levels in this composition, for example less than 5 wt % in total. The majority of these ingredients will be suitable for inclusion and are within the scope of the invention because they have negligible impact on the key properties of ocular irritation and conditioning performance. However some ingredients can adversely affect the ocular irritation potential of the composition and even the conditioning performance, e.g., alkyl sulfates and alkyl aryl sulfates used at more than a few percent, solvents, high levels of anionic polymers. As long as the % permeability of fluorescein leakage through the cell layer remains less than 10%, (or alternatively that the Zein solubility is less than 1% in the less preferred Zein Solubility In-Vitro Assay) and the maximum combing force in the Wet-Combing In-Vitro Assay is below about 25 gm-force, preferably below 22 and most preferably below 20, the optional ingredient is suitable for inclusion.

EXAMPLES

The following examples are shown as illustrations of the invention, the criticalities but are not intended in any way to limit its scope.

Example 1

This Example Illustrates the Combination of Mildness and Excellent Conditioning Performance of the Instant Compositions Examples 1A and 1 B, whose compositions are given in Table 1A were prepared as follows:

Preparation of Ex 1A (Clear 2-in-1 Composition)

A vessel was charged with water. Polymer JR 30M was dispersed in water by mixing at about 250 rpm followed by cocamidopropyl betaine. The resulting clear mixture was heated to about 60-63 C and PEG-150 distearate was added and mixed until dissolved. Heating was discontinued and cocamidopropyl hydroxysultaine was added while maintaining agitation. Sodium lauryl ethoxy (3EO) sulfate was added and mixed until dissolved. At 50 C or below, Silicone microemulsion (DC2-1870HV) was added and mixed until dissolved. The remaining ingredients consisting of sodium citrate, preservatives, fragrance, dyes and citric acid to adjust the pH to about 6.5 were added sequentially and mixed until clear and uniform.

Preparation of Ex 1B (Opacified 2-in-1 Composition)

A vessel was charged with about ⅔ amount of water. Polymer JR 30M was dispersed in water by mixing at about 250 rpm followed by Cocoamidopropyl betaine. The resulting clear mixture was heated to about 60-63 C and PEG-150 distearate was added and mixed until dissolved. Heating was discontinued and cocoamidopropyl hydroxysultaine was added while maintaining agitation. Sodium lauryl ethoxy (3EO) sulfate was added and mixed until dissolved. While surfactants were mixing, Carbopol 980 was dispersed using the remaining water in a separate vessel using high agitation of about 700 rpm. This Carbopol slurry was then added and mixed until dispersed. At 50 C or below, a premix of mica and titanium dioxide with silicone macroemulsion (DC 1786) was prepared and added. The remaining ingredients consisting of preservatives, fragrance, dyes and sodium hydroxide to adjust the pH to about 6.5 were added sequentially and mixed until uniform.

TABLE 1A

| Ingredients | Ex 1A Wt % | Ex 1B Wt % |
|---|---|---|
| Lauryl ethoxy (3EO) sulfate | 7 | 7 |
| Cocoamidopropyl betaine | 3 | 3 |
| Cocoamidopropyl hydroxysultaine | 4 | 4 |
| Carbopol 980 | | 0.6 |
| Polyquaternium-JR (30M) | 0.2 | 0.2 |
| Silicone macroemulsion containing 36% dimethiconol (DC1786) | | 1.15$^a$ |
| Silicone microemulsion containing 22% dimethiconol (DC2-1870HV) | 0.79$^a$ | |
| Mica and titanium dioxide | | 0.1 |
| PEG-150 distearate | 0.3 | 0.15 |
| Sodium Citrate | 0.5 | |
| Minors fragrance, preservatives, dyes, pH adjuster | 0.7 | 1.2 |
| Water | to 100 | to 100 |
| Appearance | Clear | Opaque |

$^a$As silicone

The performance of Ex 1A and Ex 1B in in-vitro assays of mildness, silicone deposition and wet-combing are summarized in Table 1B and are also compared with several marketed shampoo products that serve as comparative examples. These assays are described above in the EVALUATION METHODOLOGY section.

The results in Table 1B indicate that the compositions of the present invention combining an alkyl ethoxy sulfate (EO≧3), a betaine, and an hydroxysultaine in the claimed proportions with a non-volatile water-insoluble silicone and include optional but preferred cationic polymer and thickening system indeed provide mild formulation with low potential for ocular irritation and excellent hair conditioning properties.

TABLE 1B

| Assay | Ex 1A | Ex 1B | C1 | C2 | C3 |
|---|---|---|---|---|---|
| Fluorescein Leakage in-Vitro Assay (ocular irritation) % permeability | | | | | |
| Initial | 6.0 | 7.8 | | 19.3 | 3.9 |
| 24 Hrs | 1.0 | 1.0 | | 31.5 | 0.9 |
| Classification | Minimal to mild | Minimal to mild | | Moderate | Minimal to mild |
| In-vitro assay of silicone deposition | | | | | |
| Micrograms Dimethiconol per gram hair | 650 | 740 | 150 | | |
| In-vitro assay of wet combing force | | | | | |
| Maximum Load (gm-force) | 17.8 | 20.5 | 24.3 | | 26.2 |
| Total Energy (mJ) | 17.3 | 20.8 | 24.2 | | 26.1 |

C1 is L'Oreal Kids Fast Dry 2-in-1
C2 is Salon Selectives ("Don't fade on me" variant)
C3 is L'Oreal Extra Conditioning 2-in-1

The performance of Shampoo Ex 1A was also evaluated in a salon test. A salon ½ head test was conducted on 39 children age 3-8 with hair at least 3 inches at the crown. The product was stylist applied and dried with parent evaluation for wet stage and dry stage attributes. In addition to this, children were asked if they noticed a difference in sides for combing/pulling, knotting, and fragrance.

Half the head of each child was washed with shampoo Ex 1A while the other half was washed with a commercially available children's shampoo, C4.

In evaluations by parents, Ex 1A was found to be directionally easier to wet detangle and left hair less limp. Ex 1A was perceived to be significantly more gentle and was also perceived to be greater smelling. Children perceived a significant difference from side to side in combing/brushing.

Example 2

This Example Demonstrates that a Non-volatile, Water-insoluble Silicone Provides Better Performance than a Volatile Silicone or a Non-volatile, Water-Soluble Silicone in the Instant Composition Comparative examples C4, and C5, and Ex 2 whose compositions are given in Tables 2, were prepared by the procedure of Example 1A. These compositions differ only in the type of silicone that was employed. C4 includes a volatile silicone (D5), C5 uses a water-soluble silicone (BIOSIL BASICS SPQ) while Ex 2 contains the water-insoluble, non-volatile silicone of the present invention.

The results in Table 2 demonstrate that the non-volatile, water-insoluble silicone microemulsion delivers a greater level of conditioning to wet hair (lower maximum load and lower total energy) than a similar composition utilizing either a volatile silicone or a water-soluble silicone.

TABLE 2

| Ingredients | C4 Wt % | C5 Wt % | Ex 2 Wt % |
|---|---|---|---|
| Lauryl ethoxy (3EO) sulfate | 7 | 7 | 7 |
| Cocoamidopropyl betaine | 3 | 3 | 3 |
| Cocoamidopropyl hydroxysultaine | 4 | 4 | 4 |
| Polyquaternium-JR (30M) | 0.2 | 0.2 | 0.2 |
| Volatile silicone Cyclopentasiloxane (D5) | 0.75 | | |
| Water-soluble silicone Silicone Quaternium 13 (Biosil basics SPQ) | | 1 | |
| Water-insoluble non-volatile silicone Microemulsion DC2-1870HV) | | | 0/79$^a$ |
| PEG-150 distearate | 0.3 | 0.3 | 0.3 |
| Sodium Citrate | 0.5 | 0.5 | 0.5 |

TABLE 2-continued

| Ingredients | C4 Wt % | C5 Wt % | Ex 2 Wt % |
|---|---|---|---|
| Minors fragrance, preservatives, dyes, pH adjuster | 0.7 | 0.7 | 0.7 |
| Water | to 100 | To 100 | to 100 |
| Appearance | Turbid | Clear | Clear |
| In-vitro assay of wet combing force | | | |
| Maximum Load (gm-force) | 20.7 | 20.5 | 17.8 |
| Total Energy (mJ) | 20.8 | 20.6 | 17.3 |

Note:
[a] as silicone

Example 3

This Example Compares a Cationic Cellulose Polymer of the Present Invention with other Types of Cationic Polymers Comparative examples C6 and C7 and Example 3 whose compositions are given in Tables 3 were prepared by the procedure used in Example 1A with the appropriate substitution made for Polymer JR 30M. The results in Table 3 indicate that when the preferred cationic cellulose polymer of the instant invention is replaced by a cationic guar the composition becomes unstable and flocculates and loses its clarity. When the cationic cellulose is replaced by a synthetic cationic polymer, SALCARE the composition also loses clarity.

Example Ex 3 (cationic cellulose) was also compared with comparative example C7 (SALCARE—C60 a synthetic polymer comprising acrylamide and acrylamidopropyl trimonnium chloride) in both silicone deposition (in-vitro assay) and ease of wet-combing (salon test) as described above in the METHODOLOGY SECTION. It is seen from the results in Table 3 that the cationic cellulose not only provides a clear stable composition in the instant invention compared with the cationic synthetic polymer but surprisingly also greater silicone deposition which translates in practice to a significant perceivable benefit in ease of wet-combing.

TABLE 3

| Ingredients | C6 Wt % | C7 Wt % | Ex 3 Wt % |
|---|---|---|---|
| Lauryl ethoxy (3EO) sulfate | 7 | 7 | 7 |
| Cocoamidopropyl betaine | 3 | 3 | 3 |
| Cocoamidopropyl hydroxysultaine | 4 | 4 | 4 |
| Jaguar Excel (cationic guar derivative) | 0.2 | | |
| Salcare SC-60 (synthetic polymer) | | 0.2 | |
| Polymer JR 30M (cationic cellulose) | | | 0.2 |
| Silicone microemulsion containing 22% dimethiconol (DC2-1870HV) | 3.6 | 3.6 | 3.6 |
| PEG-150 distearate | 0.3 | 0.3 | 0.3 |
| Sodium Citrate | 0.5 | 0.5 | 0.5 |
| Minors fragrance, preservatives, dyes, pH adjuster | 0.7 | 0.7 | 0.7 |
| Water | to 100 | to 100 | to 100 |
| Appearance | Turbid, Flocculation Unstable | Turbid | Clear |

TABLE 3-continued

| Ingredients | C6 Wt % | C7 Wt % | Ex 3 Wt % |
|---|---|---|---|
| In-vitro assay of silicone deposition (micrograms Dimethiconol per gram hair) | — | 440 | 650 |
| Average wet-combing ranking measured in the Wet-Combing Panel Test | — | 2.1[a] | 1.4 |

Note:
[a] P value for the difference is 0.03

Example 4

This Example Illustrates the Greatly Improved Thickening Efficiencies by Combining Long Chain Fatty Esters of Propylene Glycol and Electrolytes Examples 4A through 4H whose compositions are given in Tables 4, were prepared by the methods described in Example 1. The example compositions in Table 4B demonstrate the unexpected synergistic thickening at low levels of inclusion in compositions that have a low total concentration of surfactants of the type and in the ratios specified in the instant invention (compare Ex 4F-4H with Ex 4A-4E). The stability of these clear compositions has been demonstrated by storage at 49° C. for 12 weeks.

TABLE 4A

| Ingredients | Ex 4A Wt % | Ex 4B Wt % | Ex 4C Wt % | Ex 4D Wt % | Ex 4E Wt % |
|---|---|---|---|---|---|
| Lauryl ethoxy (3EO) sulfate | 7 | 7 | 7 | 7 | 7 |
| Cocoamidopropyl betaine | 3 | 3 | 3 | 3 | 3 |
| Cocoamidopropyl hydroxysultaine | 4 | 4 | 4 | 4 | 4 |
| Polyquaternium-JR (30M) | 0.2 | 0.2 | 0.2 | 0.2 | 0.2 |
| Silicone microemulsion containing 22% dimethiconol (DC2-1870HV) | 3.6 | 3.6 | 3.6 | 3.6 | 3.6 |
| PEG-150 distearate | | 0.2 | | | |
| Sodium Citrate | | | 0.5 | | |
| Sodium Chloride | | | | 1 | 1 |
| Minors fragrance, preservatives, dyes, pH adjuster | 0.7 | 0.7 | 0.7 | 0.7 | 0.7 |
| Water | to 100 | to 100 | to 100 | to 100 | to 100 |
| Brookfield Viscosity (cps) @ 26 C, RV spindle at speed 20 rpm | 175 | 460 | 285 | 460 | 800 |

TABLE 4B

| Ingredients | Ex 4F Wt % | Ex 4G Wt % | Ex 4H Wt % |
|---|---|---|---|
| Lauryl ethoxy (3EO) sulfate | 7 | 7 | 7 |
| Cocoamidopropyl betaine | 3 | 3 | 3 |
| Cocoamidopropyl hydroxysultaine | 4 | 4 | 4 |
| Polyquaternium-JR (30 M) | 0.2 | 0.2 | 0.2 |
| Silicone microemulsion containing 22% dimethiconol (DC2-1870HV) | 3.6 | 3.6 | 3.6 |
| PEG-150 distearate | 0.2 | 0.2 | 0.2 |
| Sodium citrate | 0.5 | 1 | |

TABLE 4B-continued

| Ingredients | Ex 4F Wt % | Ex 4G Wt % | Ex 4H Wt % |
|---|---|---|---|
| Sodium chloride | | | 1 |
| Minors fragrance, preservatives, dyes, pH adjuster | 0.7 | 0.7 | 0.7 |
| Water | to 100 | to 100 | to 100 |
| Brookfield Viscosity (cps) @ 26 C., RV spin*dle at speed 20 rpm | 1440 | 3580 | 8650 |

Example 5

This Example Illustrates how the Exthoxylation Level of the Alcohol Ethoxy Sulfate and the Ratio of Alcohol Ethoxy Sulfate to Total Betaine and Hydroxysultaine are Critical to Mildness and Silicone Deposition Examples 5 and comparative example C8 and C9, whose compositions are given in Table 5, were prepared according to the methods of Example 1. A comparison of Ex 5 with C9 demonstrates that when the ratio of alcohol ethoxy sulfate to total betaine and hydroxysultaine is greater than the preferred range the in-vitro mildness and the silicone deposition level drop precipitously. In this example the drop in mildness occurs at a total level of ethoxy sulfate of 10%. Higher levels of ethoxysulfate can be present when the average degree of ethoxylation is greater than 3 provided the ratios of this component to total amphoteric is within the required range. Experience has shown that when the Zein solubility exceeds about 1% as measured by the procedure described in the METHODOLOGY section, the composition does not possess adequate mildness. Similarly, a comparison of EX 5 with comparative example C8, indicates that when the degree of ethoxylation of the alcohol ethoxy sulfate is less than 3, the Zein solubility exceeds 1% and the composition no longer has the target mildness profile.

TABLE 5

| Ingredients | Ex 5 Wt % | C8 Wt % | C9 Wt % |
|---|---|---|---|
| Lauryl ethoxy (1EO) sulfate | | 7 | |
| Lauryl ethoxy (3EO) sulfate | 7 | | 10 |
| Cocoamidopropyl betaine | 3 | 3 | 3 |
| Cocoamidopropyl hydroxysultaine | 4 | 4 | 4 |
| Polyquaternium-JR (30M) | 0.2 | 0.2 | 0.2 |
| Silicone Micro emulsion containing 22% dimethiconol (DC2-1870HV) | 3.6 | 3.6 | 3.6 |
| PEG-150 distearate | 0.3 | | 0.22 |
| Sodium Citrate | 0.5 | | 0.5 |
| Minors fragrance, preservatives, dyes, pH adjuster | 0.7 | 0.7 | 0.7 |
| Water | to 100 | to 100 | to 100 |
| Appearance | Cear | Cear | Clear |
| weight ratio of the alkyl ethoxy sulfate to the sum of the weights of betaine and hydroxysultaine | 1.0 | 1.0 | 1.43 |
| In-vitro mildness assay - % Zein solubilized | 0.94 | 1.15 | 1.47 |
| In-vitro assay of silicone deposition - Micrograms Dimethiconol per gram hair | 650 | | 470 |

Example 6

This Example Illustrates the Synergy in Silicone Deposition Arising by Combining the Betaine and Hydroxysultaine Surfactant Relative to either Component Used Alone Comparative examples C10 and C11 and Example 6, whose compositions are given in Table 6, were prepared using the procedure for Example 1. Silicone deposition was measured by the In-vitro Silicone Deposition Assay and the ease of wet-combing was measured by the Wet-Combing Panel Test both described above in the EVALUATION METHODOLOGY section.

The results in Table 6 clearly demonstrate the surprising synergy in the deposition of silicone on hair arising when the betaine and hydroxysultaine surfactants are combined in the ratios specified in the instant invention. Even more importantly this synergy also translates into a highly significant benefit in the ease of wet-combing (detangling) provided by the synergistic mixture of betaine and hydroxysultaine at the ratios disclosed herein (see last row of Table 6).

Further, as can be seen from a comparison of silicone deposition provided by Ex 6 with comparative example C9 (shown in Table 5), this synergy in deposition is lost when the ratio of alkyl ether sulfate to total betaine plus hydroxysultaine is outside the required combining ratio specified in the instant invention.

TABLE 6

| Ingredients | C10 Wt % | C11 Wt % | Ex 6 |
|---|---|---|---|
| Lauryl ethoxy (3EO) sulfate | 7 | 7 | 7 |
| Cocoamidopropyl betaine | 7 | | 3 |
| Cocoamidopropyl hydroxysultaine | | 7 | 4 |
| Polyquaternium-JR (30M) | 0.2 | 0.2 | 0.2 |
| Silicone microemulsion containing 22% dimethiconol (DC2-1870HV) | 3.6 | 3.6 | 3.6 |
| PEG-150 distearate | 0.3 | 0.3 | 0.3 |
| Sodium Citrate | 0.5 | 0.5 | 0.5 |
| Minors fragrance, preservatives, dyes, pH adjuster | 0.7 | 0.7 | 0.7 |
| Water | to 100 | to 100 | to 100 |
| Appearance | Clear | Clear | Clear |
| In-vitro assay of silicone deposition - Micrograms Dimethiconol per gram hair | 600 | 510 | 650 |
| Average wet-combing ranking measured in the Wet-Combing Panel Test (p-value of difference from Ex 6 | 2.39 p-value = <0.001 | 2.11 p-value 0.03 | 1.5 |
| % Change in Wet-Combing ranking vs untreated (ranking = 4.0) | 40% | 47% | 62% |

Example 7

This Example Illustrates a Shampoo Compositions that Contains a Blend of Optional Ingredients that do not Compromise the Low Occular Irritation Potential or the Conditioning Benefits of the Shampoo

TABLE 7

Shampoo composition

| Ingredients | Ex 7a Wt % | Ex 7b Wt % |
|---|---|---|
| Lauryl ethoxy (3EO) sulfate | 7 | 7 |
| Cocoamidopropyl betaine | 3 | 3 |
| Cocoamidopropyl hydroxysultaine | 4 | 4 |

TABLE 7-continued

Shampoo composition

| Ingredients | Ex 7a Wt % | Ex 7b Wt % |
|---|---|---|
| Polyquaternium-JR (30M) | 0.2 | 0.2 |
| Silicone microemulsion containing 22% dimethiconol (DC2-1870HV) | 3.6 | 3.6 |
| PEG-150 distearate | 0.3 | 0.3 |
| Sodium citrate | 0.5 | 0.5 |
| Glycerin | 0.5 | |
| Octylmethoxy cinnamate | 0.5 | |
| Apple (*Pyrus Malus*) Extract | 0.1% | |
| Orange (*Citrus Aurantium Dulcis*) Oil | | 0.1 |
| Ascorbic Acid (Vitamin C) | | 0.1 |
| Tetrasodium EDTA | | 0.5 |
| Acrylic acid/acrylamidomethyl propane sulfonic acid copolymer | | 0.5 |
| Minors fragrance, preservatives, dyes, pH adjuster | 0.7 | 0.7 |
| Water | to 100 | to 100 |

Example 8

This Example Illustrates Shampoo Compositions that Contain Various Ratios of Alkylethoxy Sulfate, Betaine, and Hydroxysultaine Surfactants Blends

TABLE 8

Shampoo composition

| Ingredients | Ex 8a | Ex 8b | Ex 8c | Ex 8d Wt % | Ex 8e | Ex 8f | Ex 8g |
|---|---|---|---|---|---|---|---|
| Lauryl ethoxy (3EO) sulfate | 10 | | 5 | 6 | 7 | 7 | 7 |
| Coco ethoxy (3.5 EO) sulfate | | 12 | 1 | 3 | | | |
| Lauryl ethoxy (4.0 EO) sulfate | | | | | | 5 | 7 |
| Cocoamidopropyl betaine | 7 | 6 | 3 | 4 | 6 | 5 | 4.1 |
| Cocoamidopropyl hydroxysultaine | 6.3 | 10 | 3 | 5 | 8 | 5 | 6.6 |
| Polyquaternium-JR (30M) | 0.2 | 0.3 | 0.15 | | 0.2 | 0.25 | 0.5 |
| Silicone microemulsion containing 22% dimethiconol (DC2-1870HV) | 3.6 | | | | 4.5 | 4.0 | 4.0 |
| Silicone macroemulsion containing 36% dimethiconol (DC1786) | | 3.5 | 3.5 | 2.6 | | | |
| PEG-150 distearate | | | 0.5 | 0.2 | 0.1 | 0.1 | |
| Sodium citrate | | | 0.7 | 0.6 | | 0.3 | 0.2 |
| Apple (Pyrus Malus) Extract | 0.1 | | | | | | |
| Orange (Citrus Aurantium Dulcis) Oil | | | | | | | 0.1 |
| Minors fragrance, preservatives, dyes, pH adjuster | 0.7 | 0.8 | 0.7 | 0.9 | 0.6 | 1.0 | 0.7 |
| Water | to 100 | to 100 | to 100 | to 100 | to 100 | to 100 | to 100 |
| R1 (Betaine/Hydroxysultaine Ratio) | 1.1 | 0.6 | 1.0 | 0.8 | 0.75 | 1.0 | 0.6 |
| R2 (Ethoxy sulfate/(Betaine + Hydroxysultaine) Ratio) | 0.75 | 0.75 | 1.0 | 1.0 | 0.5 | 1.25 | 1.3 |

What is claimed is:

1. A mild aqueous shampoo composition having excellent detangling and conditioning properties comprising:

i) about 6 to about 8% of an alkyl ethoxy sulfate surfactant wherein the alkyl group has an average of 12-16 carbon atoms and the degree of ethoxylation is at least 3, ii) from about 2% to about 7% of a betaine surfactant, iii) from about 2% to about 7% of a hydroxysultaine surfactant, iv) from about 0.1% to about 5% of a non-volatile, water-insoluble silicone, v) at least about 70 wt % water;

vi) less than about 2% of an added surfactant selected from the group consisting of alkyl sulfates and alkyl or alkyl aryl sulfonates, ethoxylated alkylphenols and ethanolamides of aliphatic acids;

wherein the weight ratio of the betaine surfactant to the hydroxysultaine surfactant is in the range of from about 0.5 to about 1.5, and the weight ratio of the alkyl ethoxy sulfate surfactant to the sum of the weights of betaine surfactant and hydroxysultaine surfactant is in the range of from about 0.5 to about 1.5; wherein the composition is not a potential eye irritant as measured by having either a Zein solubility of less than about 1% as measured by the Zein Solubility In-Vitro Assay or a % permeability of fluorescein leakage less than about 10% as measured by the Fluorescein Leakage Assay; and wherein the composition has a wet-combing force less than about 20 gm-force as measured by the Wet and Dry Combing Force In-Vitro Assay.

2. The composition according to claim 1, wherein the alkyl ethoxy sulfate surfactant is present at a level from about 5% to about 10% by weight of the composition.

3. The composition according to claim 1, wherein the betaine is selected from the group consisting of lauryl betaine, coco betaine, cocoamidobetaines, cocoamidopropyl betaine, oleyl betaine, caprylamidopropyl betaine, lauramidopropyl betaine, isostearylamidopropyl betaine, coco imidoazolinium betaine, and mixtures thereof.

4. The composition according to claim 1 wherein the hydroxysultaine is selected from the group consisting of alkylamidopropyl hydroxysultaine, lauryl hydroxysultaine, tallowamidopropyl hydroxysultaine, erucamidopropyl hydroxysultaine, and alkylether amidopropyl hydroxysultaine, and mixtures thereof.

5. The composition according to claim 1, wherein the non-volatile, water-insoluble silicone is a microemulsion.

6. The composition according to claim 1, wherein the non-volatile, water-insoluble silicone has a viscosity greater than 10,000 CST and is selected from the group consisting of dimethicone, dimethiconal, a cross-linked dimethicone or dimethiconal, a silicone gum, an organomodified silicone and mixtures thereof.

7. The composition according to claim 1 wherein the wt % ratio of the betaine surfactant to the hydroxysultaine surfactant is in the range of from about 0.75 to 1.25.

8. The composition according to claim 1, wherein the wt % ratio of the alkyl ethoxy ether sulfate to the sum of the betaine surfactant and the hydroxysultaine surfactant is in the range of about 0.7 to 1.3.

9. The composition according to claim 1 further comprising a cationically modified cellulose.

10. The composition according to claim 9 wherein the cationically modified cellulose is selected Polyquaterium-10.

11. The composition according to claim 1 further comprising a polyethylene glycol fatty diester selected from the group consisting of PEG 120 methyl glucoside dioleate, PEG-150 pentaerythrityl, PEG-75 dioleate, PEG-150distearate and mixtures thereof.

12. The composition according to claim 11 wherein the polyethylene glycol fatty diester is PEG 150 distearate.

13. The composition according to claim 11 further comprising an electrolyte selected form the group consisting of sodium chloride, sodium citrate, sodium sulfate, sodium bromide, sodium iodide and mixtures thereof.

14. The composition according to claim 1 further comprising aesthetic and adjunct shampoo ingredients selected from the group consisting of perfumes, pearlizing and opacifying agents, interference pigments, dyes, colorants, sensates, preservatives, thickeners, emulsion stabilizers, and mixtures thereof.

15. The composition according to claim 1 further comprising skin and hair benefit agents selected from the group consisting of cholesterol, ceramides, and pseudoceramides, non-silicone hair conditioning agents, humectants, antimicrobial agents, sunscreens, chelating agents, botanical extracts, and mixtures thereof.

16. A mild aqueous shampoo composition having excellent detangling and conditioning properties consisting essentially of:
  i) from about 6% to about 8% of an alkyl ethoxy sulfate wherein the alkyl group has an average of 12-16 carbon atoms and the degree of ethoxylation is at least 3,
  ii) from about 2% to about 7% of a betaine surfactant selected from the group consisting of alkylamido betaine, alkyl betaine, and alkyl amidoalkyl betaine,
  iii) from about 2% to about 7% of an alkylamido hydroxysultaine,
  iv) from about 0.05% to about 2% of a cationically modified cellulose,
  v) from about 0.1 % to about 5% of a non-volatile, water-insoluble silicone,
  vi) from about 0.02% to about 1.0% of a polyethylene glycol fatty diester,
  vii) from about 0.1% to about 1.0% of an electrolyte selected from the group consisting of sodium chloride, sodium citrate, sodium sulfate, sodium bromide, sodium iodide and mixtures thereof,
  viii) at least 70 wt % water;
  ix) less than about 2% of an added surfactant selected from the group consisting of alkyl sulfates and alkyl or alkyl aryl sulfonates, ethoxylated alkylphenols and ethanolamides of aliphatic acids;
  wherein the weight ratio of the betaine surfactant to the alkylamido hydroxysultaine is in the range of from about 0.5 to about 1.5, and the weight ratio of the alkyl ethoxy ether sulfate to the sum of the weights of betaine surfactant and alkylamido hydroxysultaine components is in the range of from about 0.5 to about 1.5;
  wherein the shampoo composition is not a potential eye irritant as measured by having either a Zein solubility of less than about 1% as measured by the Zein Solubility In-Vitro Assay or a % permeability of fluorescein leakage less than about 10% as measured by the Fluorescein Leakage Assay; and
  wherein the composition has a wet-combing force less than about 20 gm-force as measured by the Wet and Dry Combing Force In-Vitro Assay.

17. A method of shampooing children's hair to achieve clean, tangle-free, and conditioned hair without eye irritation said method comprising the step of treating the hair with the shampoo composition according to claim 1.

18. The composition according to claim 1 wherein the shampoo composition has a Zein solubility of less than about 1% as measured by the Zein Solubility in-Vitro Assay.

19. The composition according to claim 1 wherein the shampoo composition has a % permeability of fluorescein leakage less than about 10% as measured by the Fluorescein Leakage Assay.

* * * * *